(12) United States Patent
Kleinert et al.

(10) Patent No.: US 12,623,865 B2
(45) Date of Patent: May 12, 2026

(54) TRANSPORT SYSTEM FOR STERILE-PRODUCT TUBS AND USE OF A TRANSPORT SYSTEM

(71) Applicant: Syntegon Technology GmbH, Waiblingen (DE)

(72) Inventors: Marcus Kleinert, Wallhausen (DE); Ulrich Krauß, Ilshofen (DE); Lars Albig, Gerabronn (DE)

(73) Assignee: Syntegon Technology GmbH, Waiblingen (DE)

( * ) Notice: Subject to any disclaimer, the term of this patent is extended or adjusted under 35 U.S.C. 154(b) by 93 days.

(21) Appl. No.: 18/862,595

(22) PCT Filed: May 17, 2023

(86) PCT No.: PCT/EP2023/063274
§ 371 (c)(1),
(2) Date: Nov. 4, 2024

(87) PCT Pub. No.: WO2023/227446
PCT Pub. Date: Nov. 30, 2023

(65) Prior Publication Data
US 2025/0382141 A1 Dec. 18, 2025

(30) Foreign Application Priority Data

May 24, 2022 (DE) ..................... 10 2022 113 005.3

(51) Int. Cl.
*B65G 54/02* (2006.01)
*A61B 50/33* (2016.01)
(52) U.S. Cl.
CPC .............. *B65G 54/02* (2013.01); *A61B 50/33* (2016.02)
(58) Field of Classification Search
CPC ................................ B65G 54/02; A61B 50/33
(Continued)

(56) References Cited

U.S. PATENT DOCUMENTS 6,970,413 B2* 11/2005 Gibson ................... G11B 11/08
369/126
7,850,914 B2* 12/2010 Veiner .................... G01N 35/04
422/65
(Continued)

FOREIGN PATENT DOCUMENTS

DE 102014201967 A1 8/2015
DE 102014214697 A1 1/2016
(Continued)

OTHER PUBLICATIONS

International Search report and Written Opinion for Application No. PCT/EP2023/063274 dated Aug. 28, 2023 (24 pages including English machine translation).
(Continued)

*Primary Examiner* — Mark A Deuble
(74) *Attorney, Agent, or Firm* — Michael Best & Friedrich LLP

(57) ABSTRACT

The invention relates to a transport system for sterile-product tubs (18), having a conveyor element for arranging a sterile-product tub and having a drive for moving the conveyor element, wherein the transport system is a planar transport system (10), wherein the conveyor element is a transport platform which has a placement surface for placing a sterile-product tub that is to be transported, wherein the drive comprises a drive surface (12) to which the transport platform can be electromagnetically coupled and which can move parallel to the drive surface, and wherein the planar transport system has a first additional platform (34) which can be electromagnetically coupled to the drive surface and can be moved independently of the transport platform parallel to the drive surface, and which has at least one support element (46) assigned to the first additional platform in order
(Continued)

to support a side wall of a sterile-product tub placed on the placement surface of the transport platform.

12 Claims, 3 Drawing Sheets

(58) Field of Classification Search
USPC ......................................... 198/619, 717–721
See application file for complete search history.

(56) References Cited

U.S. PATENT DOCUMENTS

| | | | | |
|---|---|---|---|---|
| 9,079,724 B2 * | 7/2015 | van de Loecht | ..... | B65G 47/841 |
| 9,239,335 B2 * | 1/2016 | Heise | ..................... | G01N 35/04 |
| 9,878,849 B2 * | 1/2018 | Colin | .................. | B65G 54/025 |
| 9,902,572 B2 * | 2/2018 | Mahmudimanesh | .. | G01N 35/04 |
| 9,969,570 B2 * | 5/2018 | Heise | ..................... | G01N 35/04 |
| 11,226,348 B2 * | 1/2022 | Vollenweider | ......... | G01N 35/04 |
| 12,017,871 B2 | 6/2024 | Lu et al. | | |
| 2016/0077120 A1 * | 3/2016 | Riether | .................. | G01N 35/04 |
| | | | | 422/65 |
| 2018/0210001 A1 * | 7/2018 | Reza | ......................... | B01L 9/06 |
| 2018/0229866 A1 | 8/2018 | Eberhardt et al. | | |
| 2018/0265230 A1 | 9/2018 | Burk et al. | | |
| 2022/0227008 A1 | 7/2022 | Chianura et al. | | |
| 2022/0402638 A1 | 12/2022 | Mondini et al. | | |
| 2023/0146784 A1 | 5/2023 | Use et al. | | |
| 2023/0382661 A1 | 11/2023 | Dekocker et al. | | |
| 2024/0061411 A1 * | 2/2024 | Schwarz | .............. | B65G 65/005 |
| 2024/0178737 A1 | 5/2024 | Beckhoff et al. | | |
| 2025/0313419 A1 * | 10/2025 | Piccinini | ................ | B65G 54/02 |

FOREIGN PATENT DOCUMENTS

| | | | | |
|---|---|---|---|---|
| DE | 102014119351 A1 | 6/2016 | | |
| DE | 102015209618 A1 | 12/2016 | | |
| DE | 102020120282 A1 | 2/2022 | | |
| EP | 4421009 A1 * | 8/2024 | ............ | B65G 19/02 |
| FR | 3063973 A1 | 9/2018 | | |
| WO | 2019007923 A1 | 1/2019 | | |
| WO | 2020243814 A1 | 12/2020 | | |
| WO | 2021001863 A1 | 1/2021 | | |
| WO | 2021188596 A1 | 9/2021 | | |
| WO | 2022090266 A1 | 5/2022 | | |
| WO | 2023020926 A1 | 2/2023 | | |

OTHER PUBLICATIONS

Anonymous. "Planar Motor Produktentladung" Prior Art Publishing GMBH, Prior Art Publishing GMBH, Manfred-Von-Richthofen-Str. 9, 12101 Berlin Germany, Vol. www.priorartregister.com, Aug. 11, 2021 (Aug. 11, 2021), pp. 1-4 XP007024225 (8 pages including English machine translation).

German Patent Office Action for Application No. 102022113005.3 dated Apr. 3, 2023 (15 pages including English machine translation).

* cited by examiner

TRANSPORT SYSTEM FOR STERILE-PRODUCT TUBS AND USE OF A TRANSPORT SYSTEM

BACKGROUND

The invention relates to an arrangement having a transport system and having a sterile-product tub.

A transport system is known from an "ABO/ATO-automatic bag and tub opening" installation previously used by the applicant, which transport system has a conveyor element in the form of a conveyor belt that is movable along a transport path by means of a drive so that sterile-product tubs arranged on the conveyor belt can be transported along the transport path.

To receive a sterile-product tub at a first station and to transfer the sterile-product tub at a second station, it is necessary to control and monitor the location, orientation and position of a sterile-product tub on the conveyor belt. For this purpose, mechanical stops, sensors and actuators are used, for example. These components must for their part be designed and adapted to the size and shape of the sterile-product tubs to be transported.

Planar drive systems are known from XP007024225 and the subsequently published document WO 2023/020926 A1. A packaging machine is known from FR 3 063 973 A1.

SUMMARY

Proceeding from here, the object of the present invention is to create a simple and flexible transport system for sterile-product tubs.

This object is achieved by an arrangement according to the disclosure.

The transport system of the arrangement according to the invention comprises a transport platform with a placement surface for placing a sterile-product tub. The weight of the sterile-product tub presses down on the transport platform. To support the sterile-product tub laterally, a first additional platform is provided, which has a support element which, in a supporting state, interacts with a side wall of a sterile-product tub placed on the placement surface of the transport platform.

The transport platform and the first additional platform are movable independently of one another on the drive surface, and therefore the support element of the first additional platform can assume different positions relative to a sterile-product tub placed on the placement surface of the transport platform.

The transport system of the arrangement according to the invention allows any desired transport paths of the sterile-product tub to be specified simply. The course of a transport path of a sterile-product tub is freely selectable across the drive surface. The transport paths can be adapted to new transport tasks and/or to changed geometries of sterile-product tubs to be transported in a simple manner and without changing a mechanical periphery.

Planar transport systems exhibit a high degree of positioning accuracy and reliable operation. Furthermore, these planar transport systems are frictionless, since the transport platform and the first additional platform do not touch the drive surface but are spaced from the drive surface via a working gap. The transport system of the arrangement according to the invention is thus also suitable in particular for use in clean rooms, for example in pharmaceutical plants.

The first additional platform secures the sterile-product tub placed on the placement surface of the transport platform against lateral slipping. This allows the use of a flat placement surface, which is suitable for sterile-product tubs of different sizes and shapes without further adaptation.

Particularly reliable support of the sterile-product tub on the placement surface of the transport platform is achieved when the transport system has a second additional platform which can likewise be electromagnetically coupled to the drive surface and moved independently of the transport platform and independently of the first additional platform parallel to the drive surface and which has at least one support element assigned to the second additional platform in order to support the side wall of a sterile-product tub placed on the placement surface of the transport platform. The support element of the first additional platform and the support element of the second additional platform are in contact with different portions of the side wall of the sterile-product tub supported by the transport platform when the sterile-product tub is transported.

It is possible for the respective support elements of the two additional platforms to be in a pressureless contact state with the side wall of the sterile-product tub. It is preferred for the respective support elements of the two additional platforms to be in clamping engagement with the side wall of the sterile-product tub. This allows particularly reliable lateral fixing of the sterile-product tub on the placement surface of the transport platform.

According to a preferred embodiment, the side wall of a sterile-product tub placed on the placement surface has a substantially rectangular profile, the first additional platform is arranged adjacently to a first corner region of the side wall, the second additional platform is arranged adjacently to a second corner region of the side wall, and the first corner region and the second corner region are adjacent to one another or diagonally opposite one another. This allows reliable securing of the position of the sterile-product tub on the placement surface, in particular while the sterile-product tub moves along a transport path and/or when the transport platform is rotated about a vertical axis of the transport platform perpendicular to the drive surface.

The planar transport system preferably comprises a control device which controls a movement of the transport platform and a movement of the first additional platform and/or of the second additional platform. This allows mutually adapted movements of the platforms to be specified.

It is further preferred when the first additional platform is rotatable about a first rotational axis perpendicular to the drive surface and/or when the second additional platform is rotatable about a second rotational axis perpendicular to the drive surface and/or when the transport platform is rotatable about a rotational axis perpendicular to the drive surface. This allows a particularly flexible choice of different relative positions of the platforms, depending on a desired transport path and/or depending on a certain geometry of the side wall of the sterile-product tub.

It is particularly preferred when the at least one support element is rail-like and extends parallel to the drive surface. This allows gentle contact or engagement with the side wall of the sterile-product tub. At the same time, an anti-rotation means is formed in comparison with a point-like contact.

According to the invention, the support element has an L-shaped profile, which makes it possible to catch the side wall of a sterile-product tub in a corner region and thus to support the sterile-product tub in different directions (in particular all parallel to the drive surface).

It is further preferred for the at least one support element to be held on a holder, wherein a distance of the support element from the drive surface is adapted to a height of an upper boundary of the side wall of a sterile-product tub placed on the placement surface of the transport platform. This allows particularly tilt-stable support of the sterile-product tub.

The sterile products are preferably syringes, vials or carpules. It is possible and preferred for the sterile products to be nested. For nesting sterile products, holders or grids can be used, which can be or are arranged in an interior of the sterile-product tub and hold the sterile products in a state aligned relative to one another and spaced from one another.

It is further preferred when the drive surface overlaps with a functional region of at least one of the following stations, preferably with functional regions of at least two of the following stations:

unpacking station for unpacking a sterile-product tub from outer packaging and/or opening station for opening a lid portion of the sterile-product tub and/or removal station for removing sterile products from an open sterile-product tub and/or filling station for filling the sterile products and/or weighing station for weighing empty sterile products or filled sterile products and/or inserting station for inserting empty or filled sterile products into an open sterile-product tub.

A functional region of a station means a region in which the particular function of the station is realized, for example unpacking a sterile-product tub from outer packaging in the functional region of an unpacking station. The overlap between a functional region of a station and the drive surface means that the sterile-product tub, possibly with outer packaging, can remain on the transport platform for further processing of the sterile-product tub, i.e., does not have to be transferred to further transport systems. This further increases the reliability of the transport system.

The invention also relates to a preferred use of the transport system of the arrangement explained above, according to the disclosure. In the functional region of an unpacking station, these features allow a sterile-product tub, which is initially arranged laterally outside the placement surface of the transport mover, to be removed from open outer packaging of the sterile-product tub, for example from a bag cut open at the side. In order to clamp the sterile-product tub between the respective support elements of the first additional platform and the second additional platform, it is possible, by moving the additional platforms, for these support elements to be first introduced into the open outer packaging of the sterile-product tub and then moved toward one another perpendicularly to the introduction movement. After the clamped state is achieved, the additional platform can be moved counter to the introduction direction and in this way transport the sterile-product tub clamped between the support elements out of the open outer packaging, into a space above the placement surface of the transport mover. The clamped state is undone by increasing the distance of the additional platform.

BRIEF DESCRIPTION OF THE DRAWINGS

Further features and advantages of the invention form the subject matter of the following description and of the drawings of an embodiment.

In the drawings.

DETAILED DESCRIPTION

Figure 1:
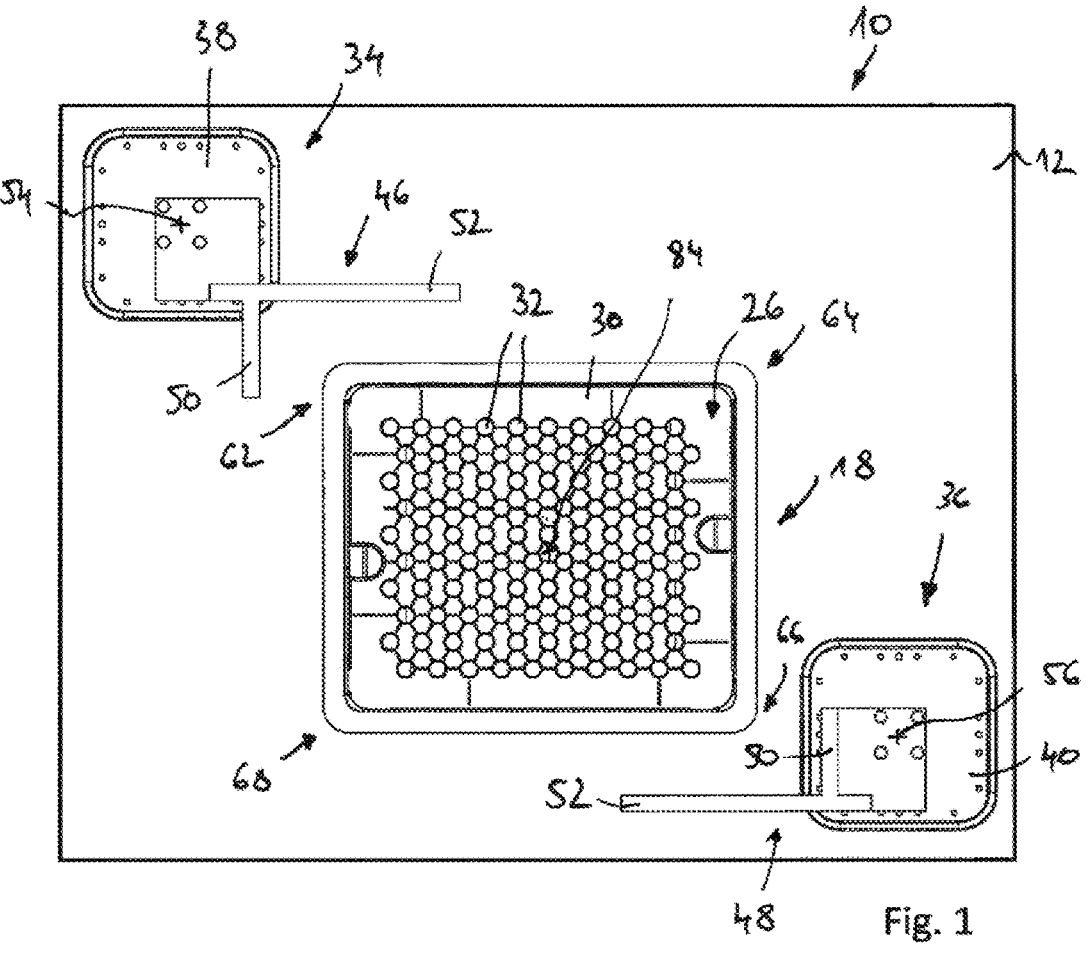
FIG. 1 shows a view from above of an embodiment of a transport system as part of an arrangement which comprises a sterile-product tub 18, in a starting state.

An embodiment of a planar transport system (referred to below as "system" for short) is labeled overall in the drawings with reference sign 10. The system 10 comprises a drive surface 12, which extends in a straight plane and is preferably oriented horizontally; cf. FIGS. 1 and 2. The drive surface 12 is used for the electromagnetic coupling and driving of a plurality of platforms, which are also referred to as "movers."

The system 10 comprises a transport platform 14 with a planar drive body 15, which has a preferably flat placement surface 16 for the placement of a sterile-product tub 18.

It is possible but not absolutely necessary for the size and geometry of the placement surface 16 to be adapted to the size and geometry of a base 20 of the sterile-product tub 18. It is also possible for the base 20 to be smaller than the placement surface 16 or to protrude laterally beyond the placement surface 16.

The sterile-product tub has a rectangular side wall 22 with an upper boundary 24, which extends along a lateral perimeter of the sterile-product tub 18 and the wall portions of which are preferably oriented perpendicularly to the drive surface 12.

The sterile-product tub 18 has an interior 26 which is laterally bounded by the side wall 22 and is closed with a lid portion 28 on a side of the sterile-product tub 18 remote from the base portion 20.

The interior 26 is used for the arrangement of a nest 30 (cf. FIG. 3), on or in which sterile products 32 are nested or held. The sterile products 32 are a plurality of syringes, vials or carpules, for example.

In addition to the transport platform 14, the system 10 comprises a first additional platform 34 and preferably also a second additional platform 36.

The additional platforms 34 and 36 each have a planar drive body 38 and 40, respectively. The drive bodies 38 and 40 can be smaller than the drive body 15 of the transport platform 14 so that a free region within which the transport platform 14 can move on the drive surface 12 is as large as possible.

The drive bodies 38, 40 are used for the arrangement of holders 42, 44, which are each connected fixedly thereto and are provided with respective support elements 46, 48 at their ends remote from the drive bodies 38, 40. The support elements 46, 48 are each rail-like and extend parallel to the drive surface 12. The support elements 46, 48 preferably have an L-shaped profile with portions 50 and 52 arranged perpendicularly to one another.

The additional platforms 34 and 36 are rotatable by corresponding actuation about respectively assigned rotational axes 54, 56, which are each oriented perpendicularly to the drive surface 12. This allows a rotary position of the support elements 46 and 48 to be set relative to a sterile-product tub 18. Preferably, the transport platform 14 is also rotatable about a rotational axis 84 oriented perpendicularly to the drive surface 12, so that an orientation of the sterile-product tub 18 can be changed simply.

Figure 2:
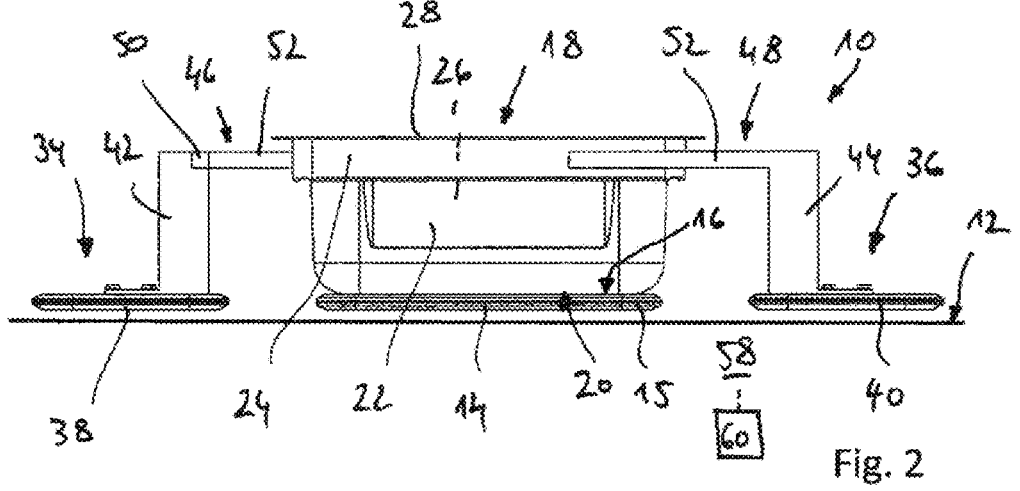
FIG. 2 shows a side view of the transport system according to FIG. 1.
Figure 4:
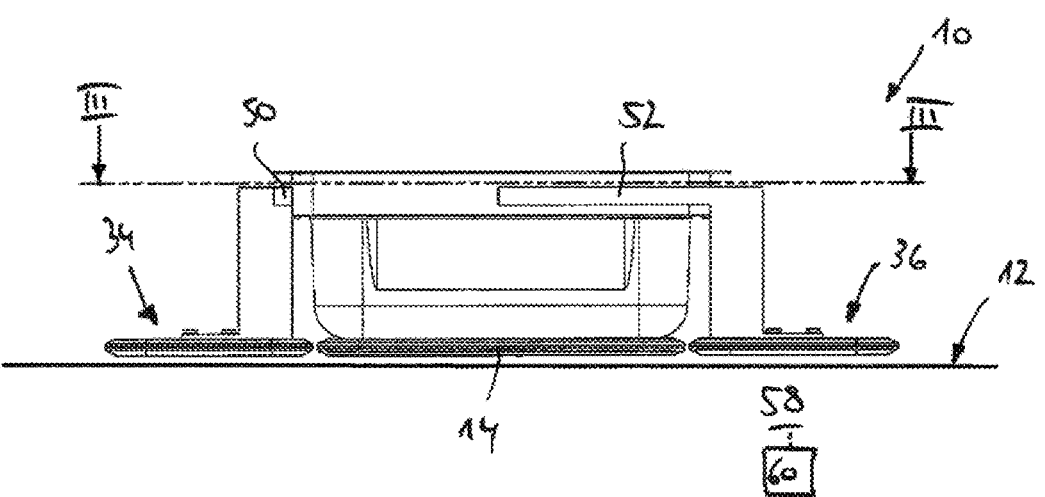
FIG. 4 shows a side view of the transport system according to FIG. 3.

The drive surface 12 is formed by a drive, which is indicated schematically with 58 in FIGS. 2 and 4 and has coils which can be energized in a manner known per se and are distributed under the drive surface 12 and generate drive energy for driving the platforms 18, 34, 36. A controller 60 is provided to control these movements.

For interaction of the additional platforms 34 and 36 with the sterile-product tub 18, it is preferred when the respective support elements 46, 48 of the additional platforms 34, 36 each interact with one of the four corner regions 62, 64, 66, 68 of the sterile-product tub 18; cf. FIG. 1, for example.

In a starting state shown in FIG. 1, the sterile-product tub 18 is placed on the placement surface 16 of the transport platform 14. The support elements 46, 48 of the additional platforms 34, 36 are initially still spaced from the side wall 22 of the sterile-product tub 18. The additional platforms 34 and 36 can then be positioned and oriented in terms of their rotary position about the rotational axes 54, 56 such that, by approaching the side wall 22 of the sterile-product tub 18, the support elements 46, 48 come into contact with the side wall 22, in particular with the upper boundary 24 of the side wall 22.

Figure 3:
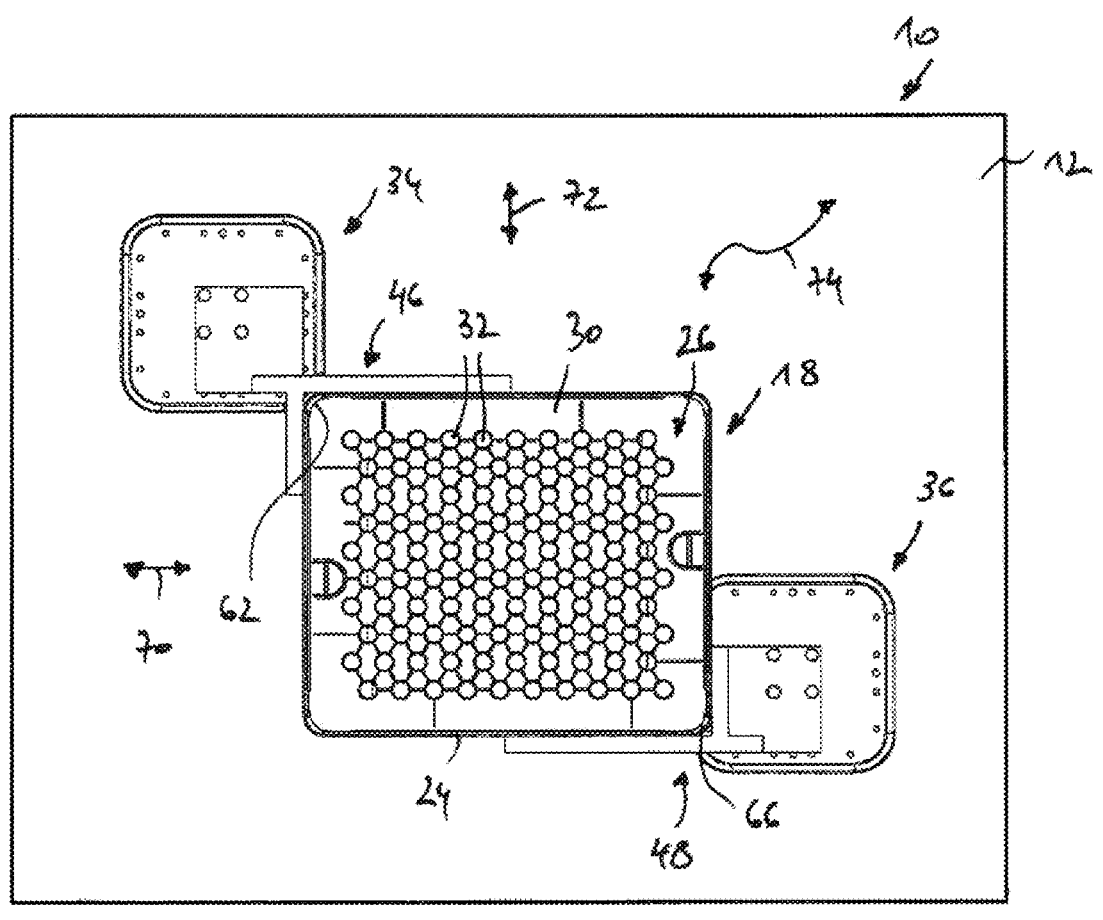
FIG. 3 shows a view from above of the transport system according to FIG. 1 along a sectional plane labeled III-III in FIG. 4, in a transporting state.

For example, it is possible for the support elements 46, 48 of the two additional platforms 34, 36 to come into engagement with mutually diagonally opposing corner regions 62 and 66 of the sterile-product tub 18 (cf. FIGS. 1 and 3). When the support elements 46, 48 are in contact with the side wall 22, it can be a pressureless contact state or else a contact with which in each case at least one of the portions 50 and 52 of both support elements 46, 48 is in clamping engagement with the side wall 22.

In each case, it is possible to transport the sterile-product tub 18 by moving the platforms 14, 34 and 36 synchronously with one another, for example along mutually perpendicular axes 70, 72 of the drive surface 12 or else at angles thereto, for example along a transport path 74 which can have any desired course within a transport plane parallel to the drive surface 12 and is indicated by way of example in FIG. 3.

Figures 5, 6:
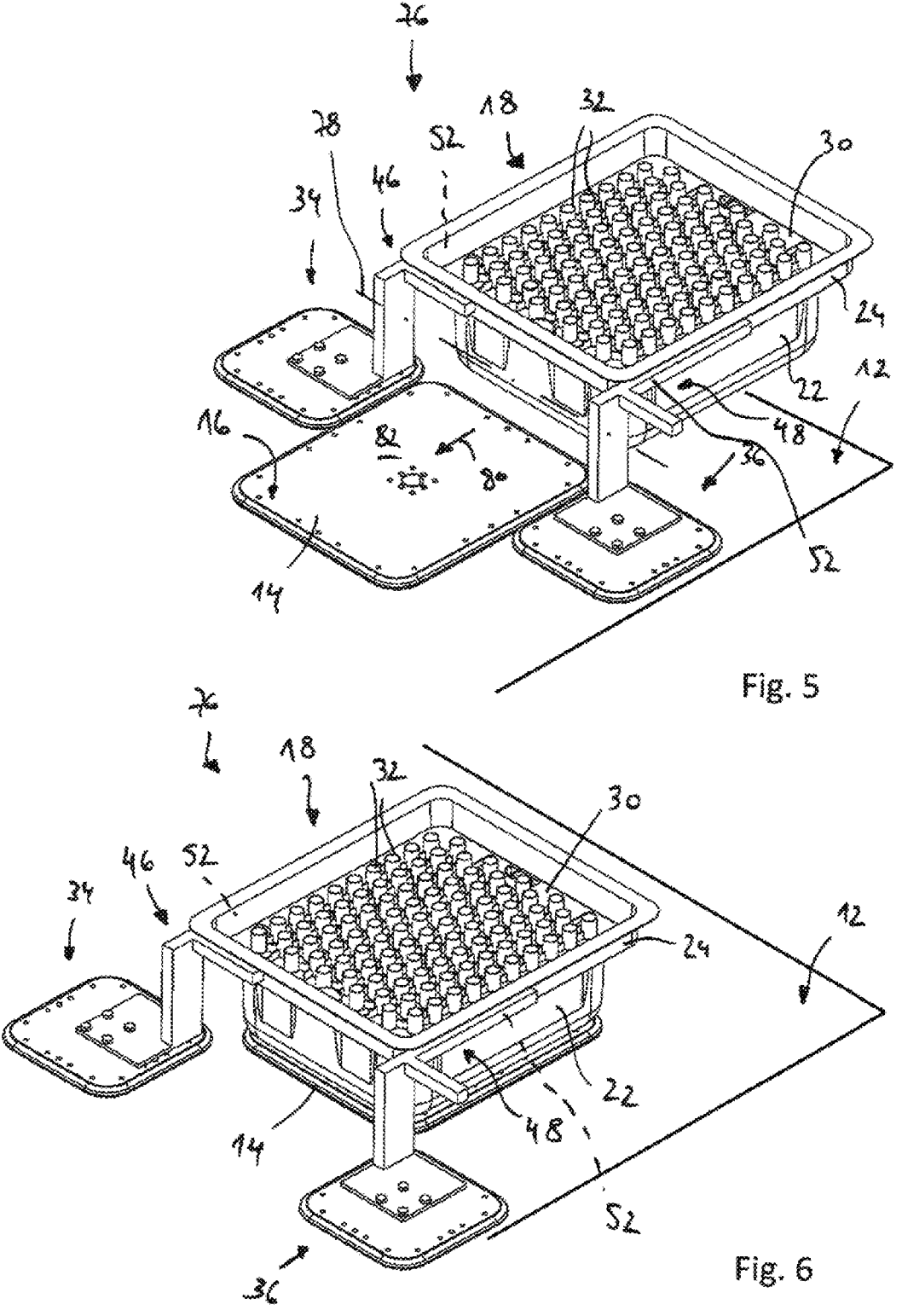
FIG. 5 shows a perspective view of the transport system according to FIG. 1 in a clamping state.
FIG. 6 shows a view corresponding to FIG. 5 in a placement state.

In this way, the sterile-product tub 18 can be brought to any station within the extent of the drive surface 12, for example to an unpacking station 76 shown in FIGS. 5 and 6. In the unpacking station 76, the sterile-product tub 18 is unpacked from outer packaging, for example in bag form (not shown). For this purpose, the outer packaging is opened by means of a cut, for example in the region of a line 78 indicated in FIG. 5 with a dash-dotted line, so that the sterile-product tub 18 can be unpacked from the outer packaging following a removal direction 80.

For the relative movement of the sterile-product tub 18 relative to the outer packaging, the support elements 46 and 48 of the additional platforms 34 and 36 are inserted into the open outer packaging (this is the state shown in FIG. 5). The additional platforms 34 and 36 are then moved toward one another parallel to the line 78 so that the respective portions 52 of the support elements 46 and 48 clamp the sterile-product tub 18 between them. The additional platforms 34 and 36 are then removed from the outer packaging together with the sterile-product tub 18 clamped therebetween, following the removal direction 80, until the sterile-product tub 18 is arranged in a space 82 above the placement surface 16 of the transport platform 14 (this is the state shown in FIG. 6, in which the base portion 20 of the sterile-product tub 18 is already touching the placement surface 16 or is arranged somewhat above it).

For the case in which the base portion 20 of the sterile-product tub 18 is already touching the placement surface 16: As a result of the increase in the distance between the platforms 34 and 36, the respective portions 52 of the support elements 46 and 48 disengage from the sterile-product tub 18, so that the sterile-product tub 18 is no longer clamped.

For the case in which the base portion 20 of the sterile-product tub 18 is arranged above the placement surface 16 (possibility 1): As a result of the increase in the distance between the platforms 34 and 36, the respective portions 52 of the support elements 46 and 48 disengage from the sterile-product tub 18, so that the sterile-product tub 18 is no longer clamped and falls onto the placement surface 16 under gravity.

For the case in which the base portion 20 of the sterile-product tub 18 is arranged above the placement surface 16 (possibility 2): It is also possible for the additional platforms 34 and 36 to be movable in a direction perpendicular to the drive surface 12 and in this way for the sterile-product tub 18 to be lowered onto the placement surface 16 in a controlled manner and only then for the distance between the platforms 34 and 36 to be increased and the clamped state undone.

The invention claimed is:

1. An arrangement having a transport system for sterile-product tubs (18) and having a sterile-product tub (18), wherein the transport system has a conveyor element for arranging the sterile-product tub (18) and a drive (58) for moving the conveyor element, wherein the transport system is a planar transport system (10), and wherein the conveyor element is a transport platform (14) which has a placement surface (16) for placing the sterile-product tub (18) that is to be transported, wherein the drive (58) comprises a drive surface (12) to which the transport platform (14) can be electromagnetically coupled and moved parallel to the drive surface (12), and wherein the planar transport system (10) has a first additional platform (34) which can be electromagnetically coupled to the drive surface (12) and moved independently of the transport platform (14) parallel to the drive surface (12) and which has at least one support element (46) assigned to the first additional platform (34) in order to support a side wall (22) of the sterile-product tub (18) placed on the placement surface (16) of the transport platform (14), wherein the at least one support element (46, 48) has an L-shaped profile, wherein the support element (46, 48) catches the side wall (22) of the sterile-product tub (18) in a corner region (62, 64, 66, 68) and supports it in different directions.

2. The arrangement as claimed in claim 1, wherein the transport system has a second additional platform (36) which can be electromagnetically coupled to the drive surface (12) and moved independently of the transport platform (14) and independently of the first additional platform (34) parallel to the drive surface (12) and which has at least one support element (48) assigned to the second additional platform (36) in order to support the side wall (22) of the sterile-product tub (18) placed on the placement surface (16) of the transport platform (14).

3. The arrangement as claimed in claim 2, wherein the side wall (22) of the sterile-product tub (18) placed on the placement surface (16) has a substantially rectangular profile, wherein the first additional platform (34) is arranged adjacently to a first corner region (62) of the side wall (22), wherein the second additional platform (36) is arranged adjacently to a second corner region (64, 66) of the side wall (22), and wherein the first corner region (62) and the second corner region (64, 66) are adjacent to one another or diagonally opposite one another.

4. The arrangement as claimed in claim 2, wherein the planar transport system (10) comprises a control device (60) which controls a movement of the transport platform (14) and a movement of the first additional platform (34) and/or of the second additional platform (36).

5. The arrangement as claimed in claim 2, wherein the first additional platform (34) is rotatable about a first rotational axis (54) perpendicular to the drive surface (12) and/or wherein the second additional platform (36) is rotatable about a second rotational axis (56) perpendicular to the drive surface (12) and/or wherein the transport platform (14) is rotatable about a rotational axis (84) perpendicular to the drive surface (12).

6. The arrangement as claimed in claim 1, wherein the at least one support element (46, 48) is rail-like and extends parallel to the drive surface (12).

7. The arrangement as claimed in claim 1, wherein the at least one support element (46, 48) is held on a holder (42, 44), wherein a distance of the support element (46, 48) from the drive surface (12) is adapted to a height of an upper boundary (24) of the side wall (22) of the sterile-product tub (18) placed on the placement surface (16) of the transport platform (14).

8. The arrangement as claimed in claim 1, wherein the sterile products (32) to be received by the sterile-product tub (18) comprise syringes, vials or carpules.

9. The arrangement as claimed in claim 1, wherein the drive surface (12) overlaps with a functional region of at least one of the following stations:

an unpacking station (76) for unpacking a sterile-product tub (18) from outer packaging, an opening station for opening a lid portion (28) of the sterile-product tub (18), a removal station for removing sterile products (32) from an open sterile-product tub (18), a filling station for filling the sterile products (32), a weighing station for weighing empty sterile products (32) or filled sterile products (32), an inserting station for inserting empty sterile products (32) or filled sterile products (32) into an open sterile-product tub (18).

10. The use of a transport system of an arrangement as claimed in claim 2 which is initially arranged laterally outside the placement surface (16) of the transport platform (14), from open outer packaging of the sterile-product tub (18), wherein the first additional platform (34) and the second additional platform (36) are arranged on mutually remote sides of the sterile-product tub (18), clamp the sterile-product tub (18) between them together with their respective support elements (46, 48), bring the sterile-product tub (18), in the clamped state thereof, into a space above the placement surface (16) of the transport platform (14), and undo the clamped state by increasing the distance between the first additional platform (34) and the second additional platform (36).

11. The arrangement as claimed in claim 8, wherein the sterile products (32) are nested.

12. The arrangement as claimed in claim 9, wherein the drive surface (12) overlaps with functional regions of at least two of the stations.

* * * * *